(12) United States Patent
Daniele et al.

(10) Patent No.: US 7,758,590 B2
(45) Date of Patent: Jul. 20, 2010

(54) CUFFED-CATHETER REMOVAL DEVICE

(76) Inventors: Anthony G. Daniele, 6008 Mason Dr., Greensburg, PA (US) 15601; Steven M. Hvozda, 1173 Amsterdam Ave., Atlanta, GA (US) 30306; Paul R. Gianneschi, 8750 Islesworth Ct., Duluth, GA (US) 30097

(*) Notice: Subject to any disclaimer, the term of this patent is extended or adjusted under 35 U.S.C. 154(b) by 849 days.

(21) Appl. No.: 11/601,743

(22) Filed: Nov. 20, 2006

(65) Prior Publication Data

US 2007/0118148 A1 May 24, 2007

Related U.S. Application Data

(60) Provisional application No. 60/738,058, filed on Nov. 21, 2005.

(51) Int. Cl.
*A61F 11/00* (2006.01)
(52) U.S. Cl. ..................................................... 606/108

(58) Field of Classification Search ................. 606/136, 606/184, 185, 167, 170, 129, 110, 159, 190, 606/108; 408/204, 206; 128/207.15; 604/174
See application file for complete search history.

(56) References Cited

U.S. PATENT DOCUMENTS

| 3,886,943 | A | * | 6/1975 | Skiff et al. | ................... | 606/159 |
| 4,955,890 | A | | 9/1990 | Yamamoto et al. | | |
| 6,361,541 | B1 | | 3/2002 | Barnhart | | |
| 6,730,096 | B2 | | 5/2004 | Basta | | |
| 2001/0047170 | A1 | * | 11/2001 | Branco | ........................ | 606/49 |
| 2006/0129134 | A1 | | 6/2006 | Kerr | | |
| 2007/0010842 | A1 | * | 1/2007 | Popov | ........................ | 606/185 |
| 2007/0185510 | A1 | | 8/2007 | Tran | | |

* cited by examiner

*Primary Examiner*—Todd E Manahan
*Assistant Examiner*—Christopher Schubert
(74) *Attorney, Agent, or Firm*—Welsh & Flaxman LLC

(57) ABSTRACT

A cuffed-catheter removal device includes a handle and a shaft extending from the handle. The shaft extends from the handle to a distal end of the cuffed-catheter removal device. At the distal end of the cuffed-catheter removal device the shaft includes a C-shaped shaft member with a concave recess shaped and dimensioned for attachment and tracking along an exposed catheter shaft.

25 Claims, 10 Drawing Sheets

FIG. 6
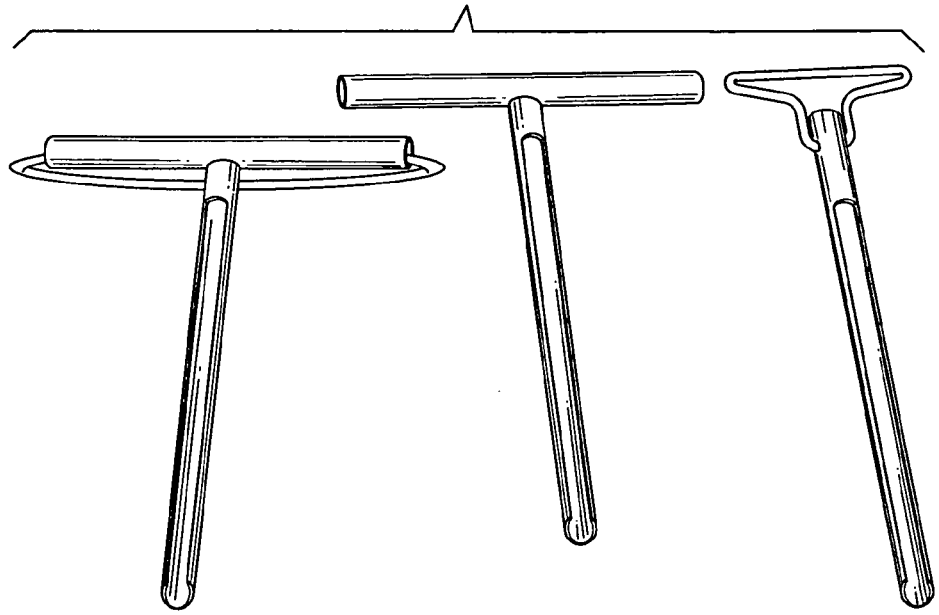
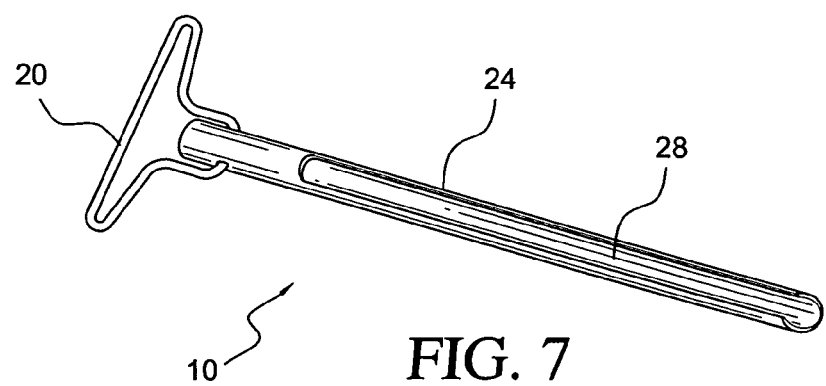
FIG. 7
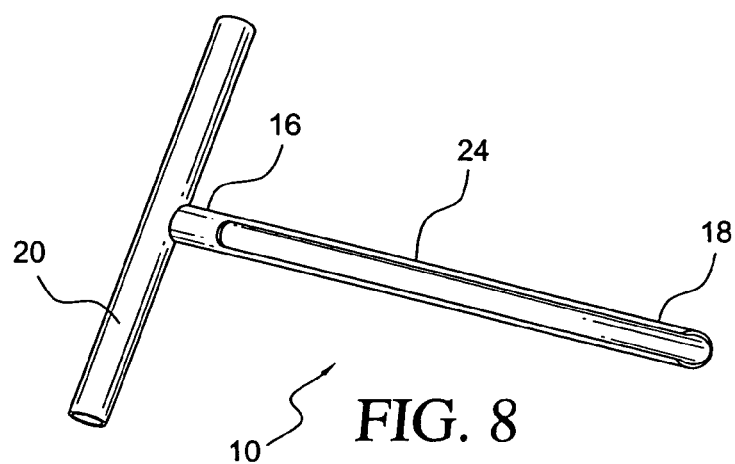
FIG. 8

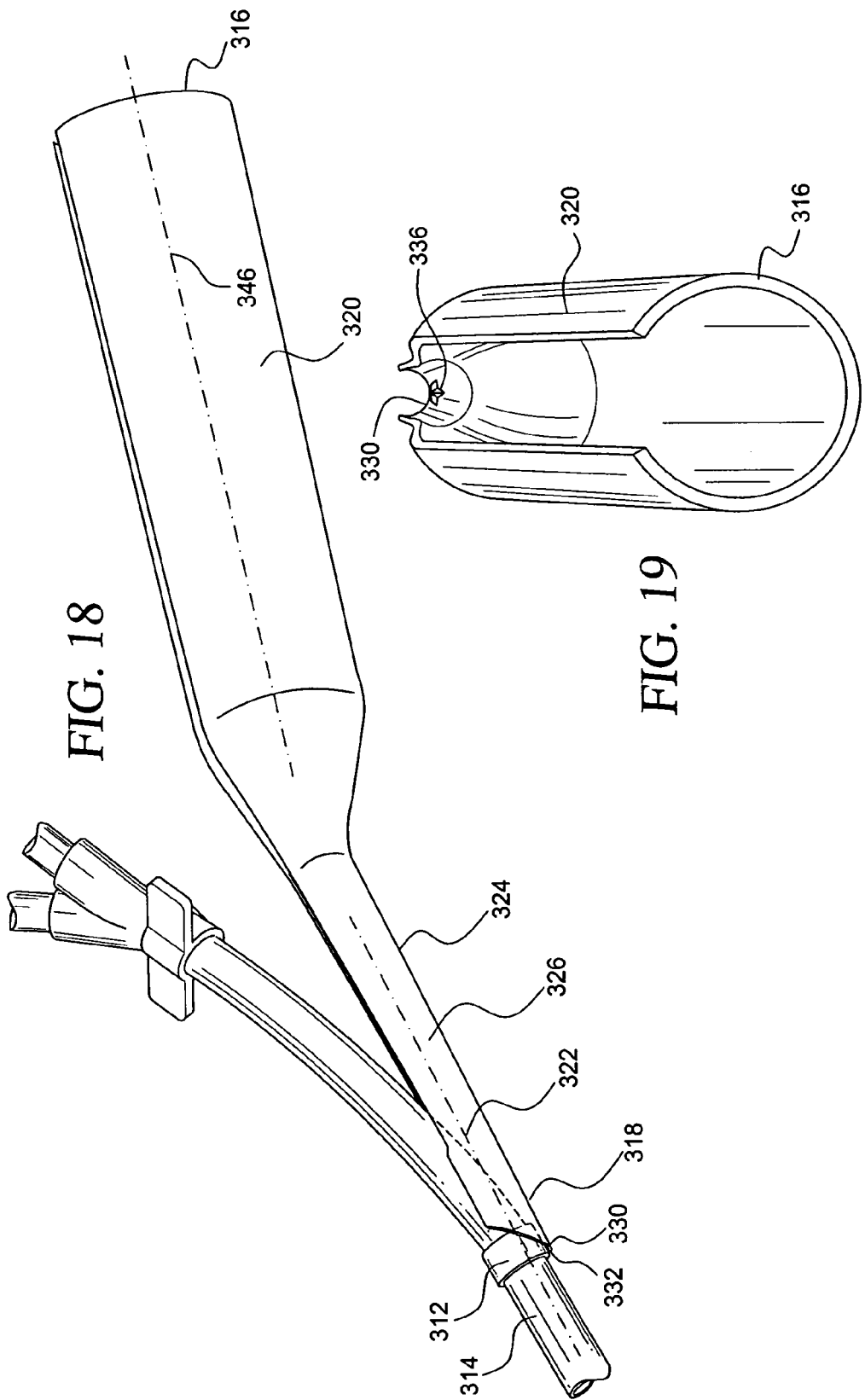

CUFFED-CATHETER REMOVAL DEVICE

CROSS REFERENCE TO RELATED APPLICATIONS

This application claims the benefit of U.S. Provisional Patent Application Ser. No. 60/738,058, entitled "CUFFED-CATHETER REMOVAL DEVICE", filed Nov. 21, 2005.

BACKGROUND OF THE INVENTION

1. Field of the Invention

The invention relates to a cuffed-catheter removal device. More particularly, the invention relates to a C-shaped cuffed-catheter removal device facilitating convenient and reliable removal of cuffed or tunneled catheters.

2. Description of the Prior Art

In the USA, there ate more than 5 million central venous catheters (CVC) inserted each year. CVCs are surgically implanted in a patient when it is necessary to deliver IV fluids, parenteral nutrition, antibiotics, chemotherapy, blood products, obtain blood samples, perform plasma pheresis and provide access for hemodialysis treatment. Central venous catheters are available in several different configurations depending upon patient indication, patient anatomy and indwelling time requirements. Specific CVC configurations are (i) PICCs (ii) Tunneled or cuffed Catheters, (iii) Ports (iv) Midline Catheters and (v) Non-tunneled Catheters.

It is estimated there are approximately 400,000 tunneled or cuffed catheters in the USA, of which 50% are used for hemodialysis treatment access. It is essential tunneled catheters be anchored within the patient. One approach to anchoring the implanted catheter is the placement of a permeable member of the implanted catheter inside the patient to promote tissue in-growth within the permeable member. Typically, the permeable member is a cuff affixed around the catheter tube. These cuffs are commercially known as "Dacron" cuffs.

Implantation of a CVC involves surgically creating a subcutaneous tunnel through the skin and into a blood vessel of the patient, and positioning the cuff midway between the skin entry point and the blood vessel entry point. After a period of time, the surrounding tissue grows into the fabric of the cuff such that the catheter is stabilized in the catheterized location. In addition, the catheterized location and the subcutaneous tunnel are sealed off, preventing foreign bodies from entering the wound and blood from exiting or pooling around the catheter near the exit site, thereby preventing patient infection. While such fabric cuffs are inexpensive to make and are generally effective at stabilizing a catheter, they are also difficult to remove. A common eventuality is that each and every catheter cuff will need to be carefully extracted from the subcutaneous channel to allow for catheter removal from the patient.

In order to remove a catheter from the ingrown subcutaneous tissue, the physician must surgically dissect around the cuff with a scalpel, cutting the subcutaneous tissue surrounding all edges of the cuff into which tissue has grown. Tissue growth occurs substantially transverse to the longitudinal axis of the cuff and around the outer circumference of the cuff In addition, tissue growth occurs at angles oblique to the longitudinal axis of the cuff along both of the cuffs side edges. The physician must cut around the circumference of the cuff and both side edges to completely detach the cuff and free the indwelling catheter.

This is a difficult and time-consuming surgical procedure that tends to result in increased patient bleeding. Prolonged surgical time also increases the risk of infection. The procedure may also contribute to an increased chance of scar tissue build-up within the subcutaneous tissue such that creation of additional subcutaneous catheter tunnels becomes increasingly difficult. Also, because cuffs are sized to provide a snug fit in the subcutaneous area, they are difficult to extract smoothly through the tunnel.

With catheters formed of softer durometer materials, such as urethane and silicone, for example, the risk that the catheter will snap or break apart during the removal procedure increases. The use of such materials also increases the risk the affixed cuff will tend to result in the elongation of the tube and alter its dimensions while placing traction. The stress placed on the proximal end of the catheter during removal from the tunnel is concentrated at the location of the cuff. If the catheter breaks during removal, the physician may have to perform a further procedure to remove the severed distal portion of the catheter left within the patient.

As mentioned above, following tissue in-growth into the CVC cuff, catheters can be removed from the subcutaneous tunnel using one of several techniques. The method used depends upon physician preference and the amount of tissue/cuff in-growth that is present. In some cases, the catheter can be removed by placing traction on the external catheter segment. However, surgical removal is commonly necessary to prevent breaking the catheter if the catheter does not dislodge easily with traction.

Current procedure options for the removal of a cuffed or tunneled CVC are traction removal, blunt dissection and surgical removal. Traction removal involves pulling the external catheter segment downward in a straight line away from the exit site with a series of gentle tugs. When separation of the cuff from the surrounding tissue and/or catheter occurs, there will be a "break-away" feeling. Continuous pulling on the catheter is required to complete the removal. In addition, pressure is applied to the catheter/vein insertion site as needed to control bleeding. If the cuff remains in the subcutaneous tissue, it must be dissected out through a small incision utilizing local anesthesia.

With regard to blunt dissection or removal, the external catheter and the entire subcutaneous catheter course are prepped and draped. Local anesthesia is administered at the exit site and around the cuff site. The position of the cuff is located either by palpation or by observing the position of "dimpling" when traction is applied to the catheter's external segment. Blunt dissection is used to widen the exit site and subsequently to disrupt the fibrin in-growth around the Dacron cuff. This is done initially with a hemostat or blunt needle. It is important to dissect the adherent fibrin sheath, which can be extremely difficult. Practitioners must avoid the use of a scalpel to remove this sheath as this can result in puncture or fragmentation of the catheter, which can subsequently result in catheter or air embolization (in the worst case scenario). In extremely stubborn catheter removal, it is wise to place a wire through the catheter and into the inferior vena cava. Therefore, if for some reason the catheter breaks, it remains on the wire and can't embolize into the heart. Subsequently, it can be retrieved in a controlled fashion using a snare. Once removal using this technique is achieved, pressure is applied to the catheter/vein insertion site as needed to control bleeding and the incision is closed with a suture as needed.

Where surgical removal is employed, the external catheter and the entire subcutaneous catheter course are prepped and draped. Local anesthesia is then administered at the exit site and around the cuff site. The position of the cuff is located either by palpation or by observing the position of "dimpling"

when traction is applied to the catheter's external segment. A scalpel is used to dissect tissue in-growth around the Dacron cuff. This must be done carefully so as not to cause significant bleeding and possible catheter dissection which can subsequently result in catheter or air embolization. As with blunt dissection, in an extremely stubborn catheter removal, it is wise to place a wire through the catheter and into the inferior vena cava. Therefore, if for some reason the catheter breaks, it remains on the wire and can't embolize into the heart. Subsequently it can be retrieved in a controlled fashion using a snare. Once the removal is complete, pressure is applied to the catheter/vein insertion site as needed to control bleeding and the incision is closed with a suture as needed.

With the foregoing in mind, a need exists for a removal technique and apparatus overcoming the shortcomings of the prior art. The present invention provides such an apparatus and associated technique.

SUMMARY OF THE INVENTION

It is, therefore, an object of the present invention to provide a cuffed-catheter removal device. The device includes a handle and a shaft extending from the handle. The shaft extends from the handle to a distal end of the cuffed-catheter removal device. At the distal end of the cuffed-catheter removal device the shaft includes a C-shaped shaft member with a concave recess shaped and dimensioned for attachment and tracking along an exposed catheter shaft.

It is also an object of the present invention to provide a cuffed-catheter removal device including a cutting edge at a leading end of the distal end of the cuffed-catheter removal device.

It is also another object of the present invention to provide a cuffed-catheter removal device wherein the C-shaped shaft member forms a substantial portion of the shaft.

It is also a further object of the present invention to provide a cuffed-catheter removal device wherein the C-shaped shaft member has a diameter slightly larger than the shaft diameter of the cuffed-catheter to be removed.

It is still a further object of the present invention to provide a cuffed-catheter removal device further including an inner bead adjacent to a distal tip of the C-shaped shaft member.

It is yet a further object of the present invention to provide a cuffed-catheter removal device wherein the inner bead is formed along an inner surface of the C-shaped shaft member.

It is another object of the present invention to provide a cuffed-catheter removal device wherein the inner bead includes a central protrusion and cutting members extending from the opposite sides of the central protrusion.

It is still another object of the present invention to provide a cuffed-catheter removal device wherein the central protrusion of the inner bead extends into a center of the C-shaped shaft member a distance of approximately 1 mm to approximately 5 mm.

It is also another object of the present invention to provide a cuffed-catheter removal device wherein the cutting members extend laterally relative to a longitudinal axis of the C-shaped shaft member.

It is also an object of the present invention to provide a cuffed-catheter removal device including a distally directed cutting member.

It is a further object of the present invention to provide a cuffed-catheter removal device wherein the C-shaped shaft member includes a slightly sharpened bevel formed along an interior surface of the C-shaped shaft member.

It is another object of the present invention to provide a cuffed-catheter removal device wherein the bevel protrudes at approximately a 45° angle relative to a longitudinal axis of the cuffed-catheter removal device.

It is also an object of the present invention to provide a cuffed-catheter removal device wherein the C-shaped shaft member includes inwardly directed flanges adjacent to the distal end of the cuffed-catheter removal device to create an inward taper.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 6, 7 and 8 show various handle constructions contemplated in accordance with the present invention.

FIGS. 17, 18 and 19 show yet another embodiment in accordance with the present invention.

DESCRIPTION OF THE PREFERRED EMBODIMENTS

Figure 1:
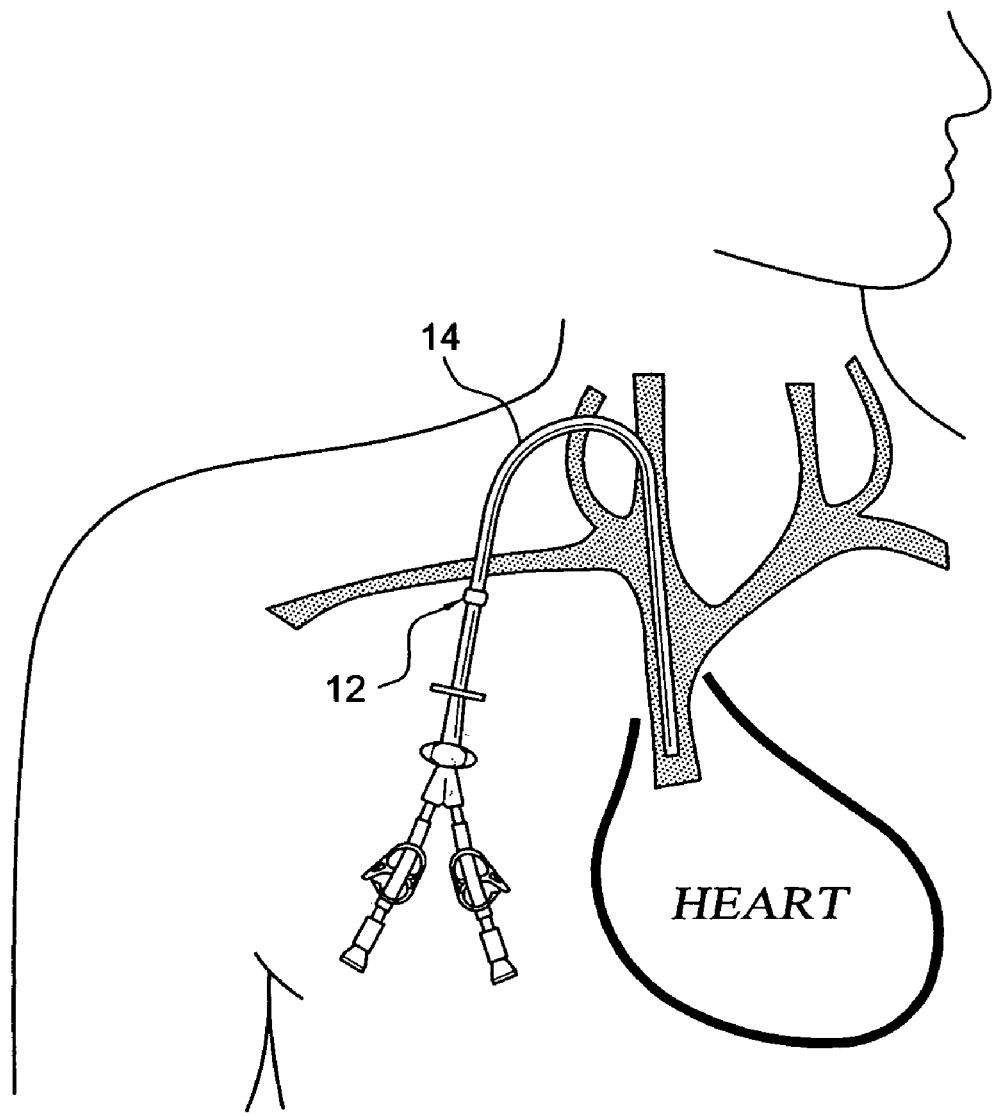
FIG. 1 is a schematic of a cuff and catheter within an individual's vascular system.
Figure 2:
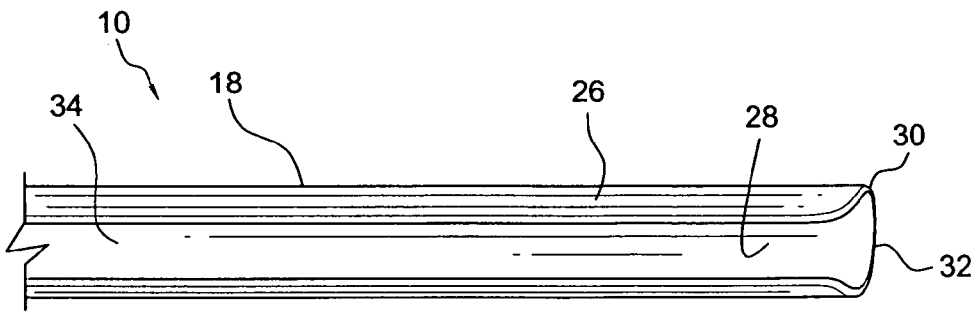
FIGS. 2, 3 and 4 are respectively a top plan view, side perspective view and alternate side perspective view of a cuffed-catheter removal device in accordance with the present invention.
Figure 3:
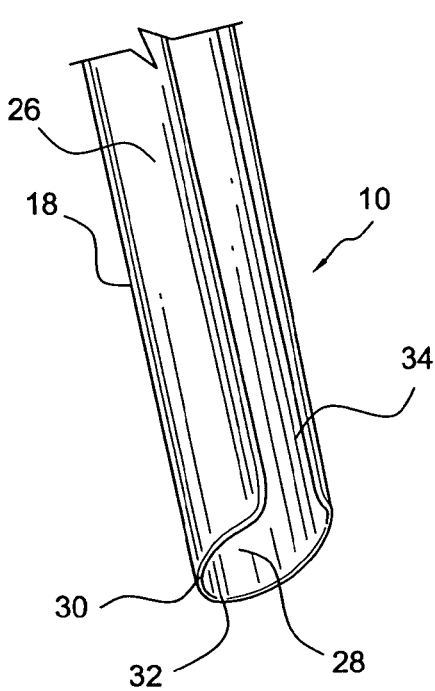
Figure 4:
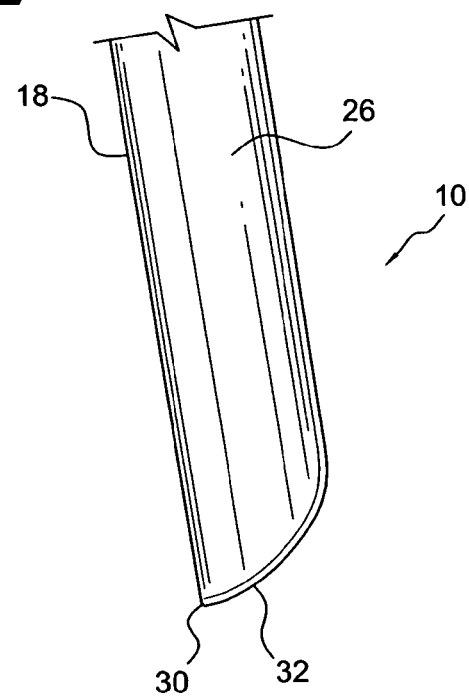
Figure 5:
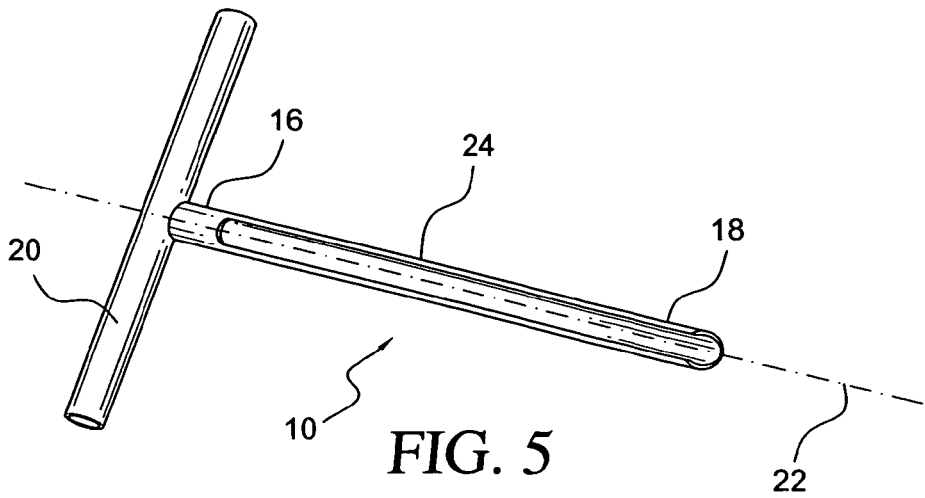
FIG. 5 is a top perspective view of the present cuffed-catheter removal device.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for teaching one skilled in the art how to make and/or use the invention.

With reference to FIGS. 1 through 11, a cuffed-catheter removal device 10 is disclosed. The cuffed-catheter removal device 10 is designed to dissect or disrupt the fibrous tissue from the cuff 12 of a tunneled cuffed-catheter (for example, a CVC) 14. Through implementation of the present cuffed-catheter removal device 10, removal time is significantly decreased. The present cuffed-catheter removal device 10 further allows removal of the catheter 14 through a preexisting pathway and precludes the need for a "cut down", utilizing a scalpel or other sharp instrument, so as to keep with a minimally invasive philosophy.

Although the present invention is disclosed for use in conjunction with a preferred cuffed-catheter, those skilled in the art will appreciate the present invention may be used in conjunction with a variety of cuffed-catheters, for example, Pleurex catheters, Tenkoff catheters and peritoneal dialysis catheters, without departing from the spirit of the present invention.

The cuffed-catheter removal device 10 generally includes a proximal end 16 and a distal end 18. The proximal end 16 includes an ergonomic handle 20 adapted for effectively allowing a practitioner to rotate the cuffed-catheter removal device 10 about 360° or more so as to circumferentially dissect the cuff 12 and catheter 14 from the surrounding tissue. In accordance with various embodiments, the ergonomic handle 20 at the proximal end 16 may take the form of a bucket handle design 20 as shown in FIGS. 6 and 7 or a T handle design 20 as shown in FIGS. 6 and 8 (where the similar reference numerals are used for similar components). Both of these handle 20 designs allow a user to readily grasp the cuffed-catheter removal device 10 and rotate the same about the longitudinal axis 22 of the cuffed-catheter removal device 10. While a bucket handle and T handle are disclosed in accordance with a preferred embodiment, other handle designs, for example, a screwdriver type handle, may be employed without departing from the spirit of the present invention.

A shaft 24 extends from the proximal end 16 of the cuffed-catheter removal device 10 to the distal end 18 of the cuffed-catheter removal device 10. The shaft 24 is adapted to extend from the proximal end 16 of the cuffed-catheter removal device 10 to the catheter cuff 12 requiring removal. At the distal end 18 of the cuffed-catheter removal device 10 the shaft 24 becomes a C-shaped shaft member 26 with a concave recess 28 shaped and dimensioned for attachment and tracking along the exposed catheter shaft (for example, a CVC shaft), with the catheter shaft positioned within the concave recess 28. In accordance with a preferred embodiment, the dimensions need to be in keeping with the CVC shaft dimensions. As those skilled in the art will appreciate, there are varying CVC shaft dimensions and, accordingly, there will also be varying cuffed-catheter device dimensions to fit associated CVCs. For example, the standard dialysis catheter diameters are 14 F to 16 F and other Hickman type design catheters are 8 F to 12 F in diameter. Dimensions such as these will be kept in mind while optimizing the dimensions of the concave recess. The leading end, or distal tip, 30 at the distal end 18 of the cuffed-catheter removal device 10 is preferably provided with a serrated or beveled cutting edge (or other cutting edge design) 32 sharp enough to dissect the fibrous tissue, but blunt enough so as to not cause catheter 14 damage.

More particularly, the C-shaped shaft member 26 forms a substantial portion of the shaft 24 extending from the handle 20 to the distal end 18 of the cuffed-catheter removal device 10. It is believed the extended length of the C-shaped shaft member 26 improves tracking of the exposed catheter 14 by allowing the catheter 14 to ride within the concave recess 28 for an extended length thereof as the cuffed-catheter removal device 10 is moved to the location of the cuff 12 requiring removal. It is contemplated in accordance with a preferred embodiment that the entire length of the shaft extending from the handle will be approximately 4 cm to approximately 12 cm, and that the concave recess may extend the entire length of the shaft or a portion thereof.

Tracking is improved by forming the C-shaped shaft member 26 in a substantially C-shape when viewed in the cross section defining the distal concave recess 28 of the distal end 18. By forming the C-shaped shaft member 26 in this manner the distal end 18 may readily track over the exposed portions of the catheter 14 with the catheter 14 extending through the opening 34 of the concave recess 28 as the cuffed-catheter removal device 10 is moved along the catheter 14 toward the predetermined cuff 12 location requiring removal.

The opening 34 of the C-shaped shaft member 26, and concave recess 28, is preferably approximately 15% to approximately 50% of the circumference of the catheter it is removing. This circumference is sufficient for passage of the catheter 14 therethrough as the cuffed-catheter removal device 10 is moved therealong. With this in mind, the C-shaped shaft member 26 defines an arc of approximately 180° to approximately 300°, wherein the opening 34 amounts approximately 60° to approximately 180° of the entire circle defined at the distal end 18 of the cuffed-catheter removal device 10.

Although specific dimensional parameters are disclosed above with reference to a preferred embodiment of the present invention, those skilled in the art will appreciate these dimensions may be varied to suit specific applications without departing from the spirit of the present invention.

Figure 9:
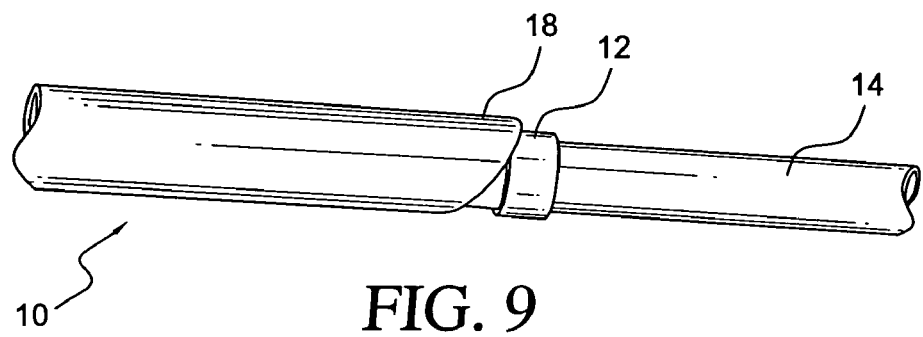
FIGS. 9, 10 and 11 show removal of a cuffed-catheter in accordance with the present invention.
Figure 10:
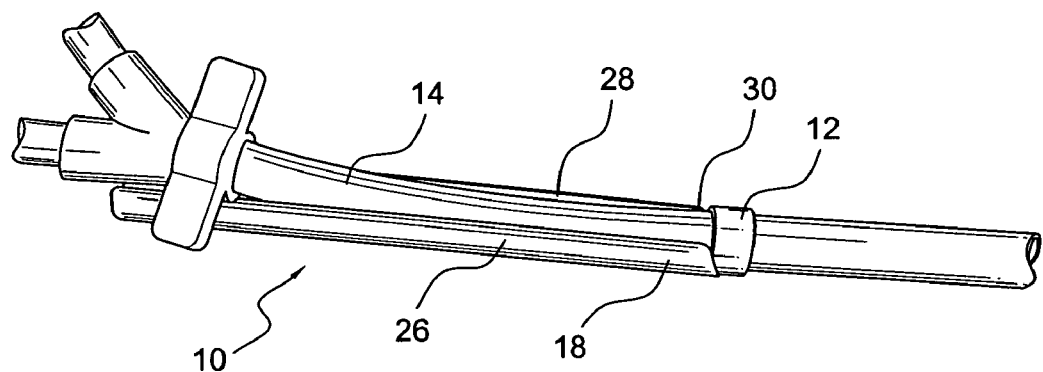
Figure 11:
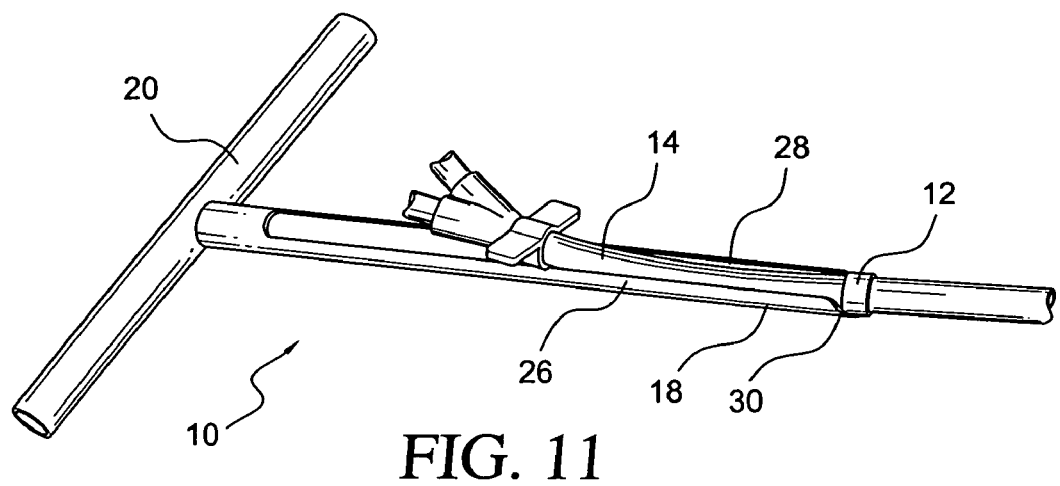

In practice, and with reference to FIGS. 9, 10 and 11, the concave recess 28 of the C-shaped shaft member 26 of the present cuffed-catheter removal device 10 is placed over the proximal or exposed end of the catheter 14 shaft and is gently pushed forward (while pulling the proximal end of the catheter 14 taut) tracking through the subcutaneous tract and is gently rotated 360° around the catheter 14 and then advanced over the catheter cuff 12. Once over the cuff 12, the cuffed-catheter removal device 10 is again gently rotated 360° around the catheter 14 circumferentially while performing short, rapid in-out motions while applying pressure on the cuffed-catheter removal device 10 directed toward the catheter 14 to dissect the cuff 12 from the surrounding tissue.

Figure 12:
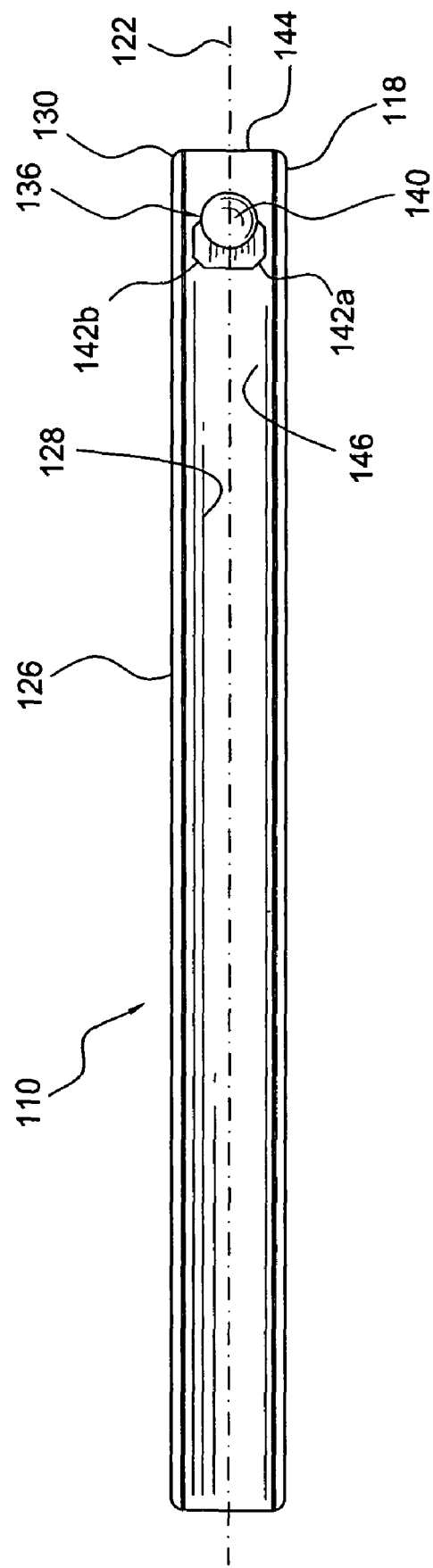
FIGS. 12, 13 and 14 show an alternate embodiment of the present cuffed-catheter removal device.
Figure 13:
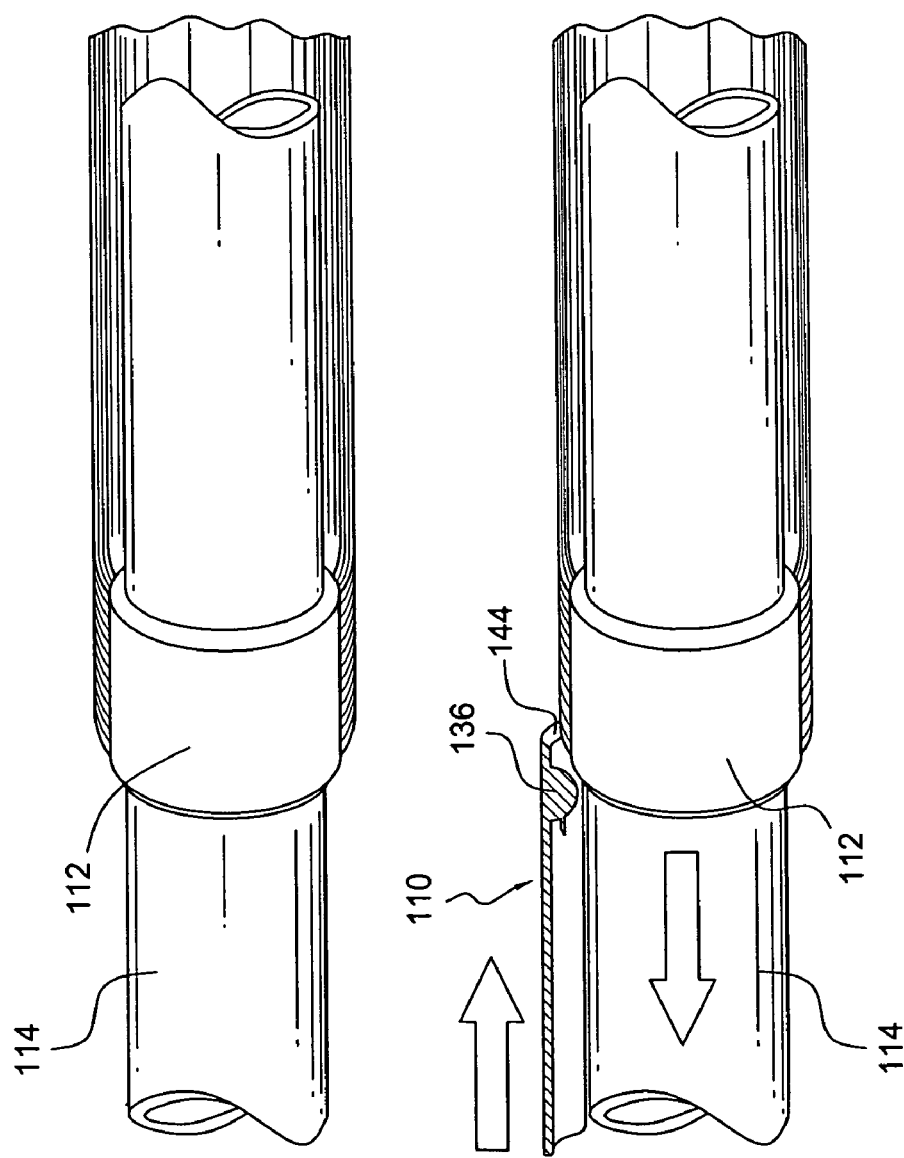
Figure 14:
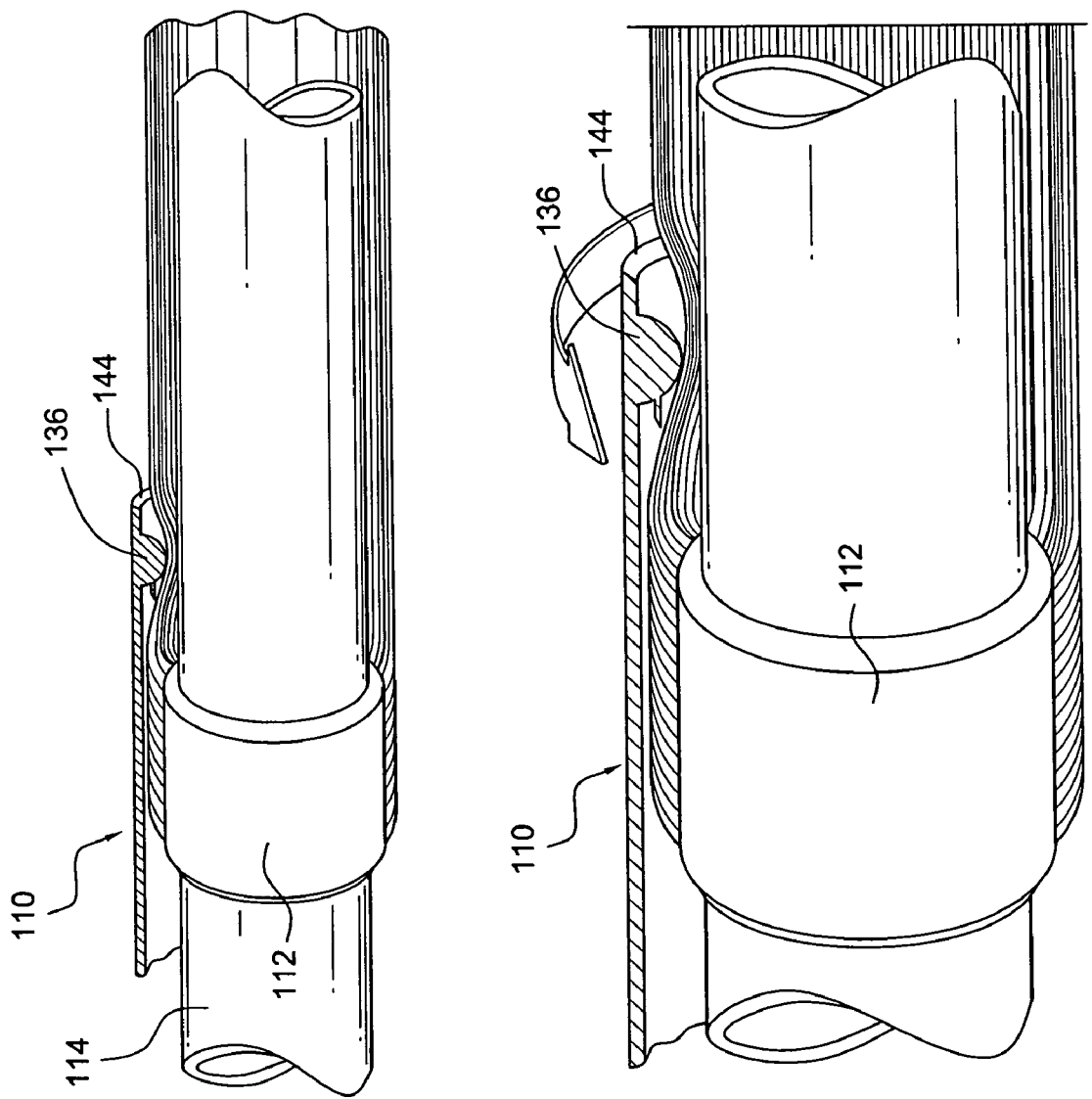

In addition, and in accordance with an alternate embodiment shown in FIGS. 12, 13 and 14, the distal end 118 of the cuffed-catheter removal device 110 may be provided with an inner bead 136 adjacent the distal tip (or leading end) 130 of the C-shaped shaft member 126, and extending inwardly within the concave recess 128. The inner bead 136 may be blunt or incorporate a sharpened edge or blade. The inner bead 136 improves removal of the cuff 112 by engaging and incising the cuff 112 for removal thereof.

More particularly, the inner bead 136 is formed along the inner surface 138 of the C-shaped shaft member 126 at a position centered along the arc defining the concave recess 128. The inner bead 136 is approximately 2 mm to approximately 20 mm from the distal tip 130 of the C-shaped shaft member 126. The inner bead 136 includes a central protrusion 140 extending into the center of the concave recess 128 a distance of approximately 1 mm to approximately 5 mm. Cutting members 142a, 142b extend from the opposite sides of the central protrusion 140. The cutting members 142a, 142b extend in a direction substantially laterally to the central longitudinal axis 122 of the C-shaped shaft member 126 while also extending about the central longitudinal axis 122 of the C-shaped shaft member 126.

The inclusion of the inner bead 136 assists in the cuff 112 removal process in two ways. First the central protrusion 140 is shaped and dimensioned to "engage" the fibrous tissue that is attached to the distal edge of the cuff 112, allowing one to exert tension on the fibrous tissue by pulling the catheter 114 proximally once the inner bead 136 of the cuffed-catheter removal device 110 is properly positioned at the desired distal edge cuff position. As such, it is contemplated the device will work best if the raised cutting members 142a, 142b on the inner bead 136 projecting from the bottom of the inner bead 136 are angled slightly toward the posterior. With the fibrous tissue 112 tensioned through the application of proximal pulling, the cuffed-catheter removal process is improved. In addition, the cutting members 142a, 142b are shaped and dimensioned to assist in cuffed-catheter removal by cutting through the fibrous tissue as the cuffed-catheter removal device 110 is rotated.

In practice, and with reference to FIGS. 13 and 14, in accordance with this embodiment the concave recess 128 of the C-shaped shaft member 126 of the present cuffed-catheter removal device 110 is placed over the proximal or exposed end of the catheter 114 and is gently pushed forward (while pulling the catheter 114 proximal end taut) tracking through the subcutaneous tract and gently rotated 360° around the catheter 114 while advancing over the catheter cuff 112, the cuffed-catheter removal device 110 is again gently rotated 360° around the catheter 114 circumferentially while performing short, rapid in-out motions while applying pressure on the device directed toward the catheter 114 allowing the cutting members 142a, 142b and beveled cutting edge 144 to dissect the cuff 112 from the surrounding tissue.

Thereafter, the present cuffed-catheter removal device 110 is advanced approximately 5 mm distal to the cuff 112 and then the cuffed-catheter removal device 110 is gently pulled back while performing short, rapid in-out and/or rotational motions while applying pressure on the device 110 directed toward the catheter 114 such that the cutting member 142a, 142b engage the tissue. All the while, traction is maintained on the catheter 114. The slightly sharpened beveled cutting edge 144 that protrudes at approximately a 45° angle and the cutting members 142a, 142b that protrude from the interior concave surface 146 of the C-shaped member 126 will now engage the fibrous tissue on the distal edge of the cuff 112 which will allow for the dissection of fibrous tissue from this edge. Again, the present cuffed-catheter removal device 110 is gently rotated 360° around the catheter 114 to circumferentially dissect the surrounding tissue. The practitioner then gently pulls back both the central venous catheter 114 and the present cuffed-catheter removal device 110 simultaneously and removes them from the patient.

Figure 15:
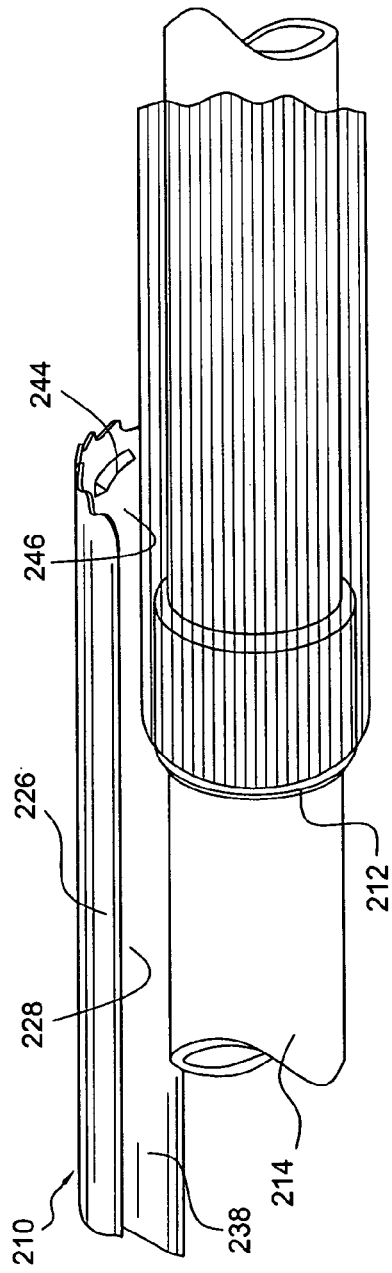
FIGS. 15 and 16 show yet another embodiment of the present cuffed-catheter removal device.
Figure 16:
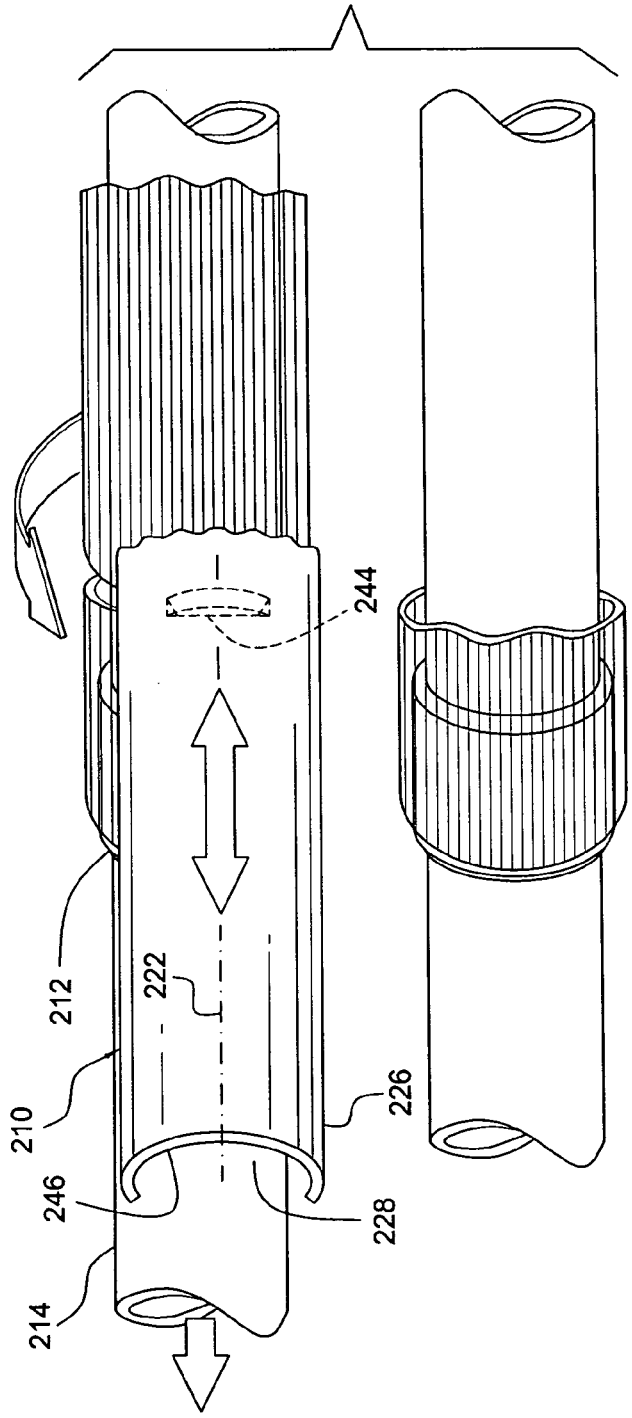

Additionally, and in accordance with a further embodiment shown in FIGS. 15 and 16, located on the interior concave surface 238 of the concave recess 228 of the cuff-catheter removal device 210, is a slightly sharpened bevel 244 that protrudes at approximately a 45° angle (or some other angle), relative to the longitudinal axis 222, which will allow for the dissection of fibrous tissue from the distal portion of the cuff 212. The cutting edge of the bevel 244 must avoid cutting the catheter 214.

In practice, and in accordance with this embodiment, the concave recess 228 of the C-shaped shaft member 226 of the present cuffed-catheter removal device 210 is placed over the proximal or exposed end of the catheter 214 and is gently pushed forward (while pulling the catheter 214 proximal end 216 taut) tracking through the subcutaneous tract and gently rotated 360° around the catheter 214, while advancing over the catheter cuff 212, the cuffed-catheter removal device 210 is again gently rotated 360° around the catheter circumferentially while performing short, rapid in-out motions while applying pressure on the device directed toward the catheter 214 to dissect the cuff 212 from the surrounding tissue.

Thereafter, the present cuffed-catheter removal device 210 is advanced approximately 5 mm distal to the cuff 212 and then the cuffed-catheter removal device 210 is gently pulled back while performing short, rapid in-out and/or rotational motions while applying pressure on the device 210 directed toward the catheter 214. All the while, traction is maintained on the catheter 214. The slightly-sharpened bevel 244 that protrudes at a 45° angle (or some other angle) located on the interior concave surface 246 of the C-shaped member 226 will now engage the fibrous tissue on the distal edge of the cuff 212 which will allow for the dissection of fibrous tissue from this edge. Again, the present cuffed-catheter removal device 210 is gently rotated 360° around the catheter 214 to circumferentially dissect the surrounding tissue. The practitioner then gently pulls back both the central venous catheter 214 and the present cuffed-catheter removal device 210 simultaneously and removes them from the patient.

Figure 17:
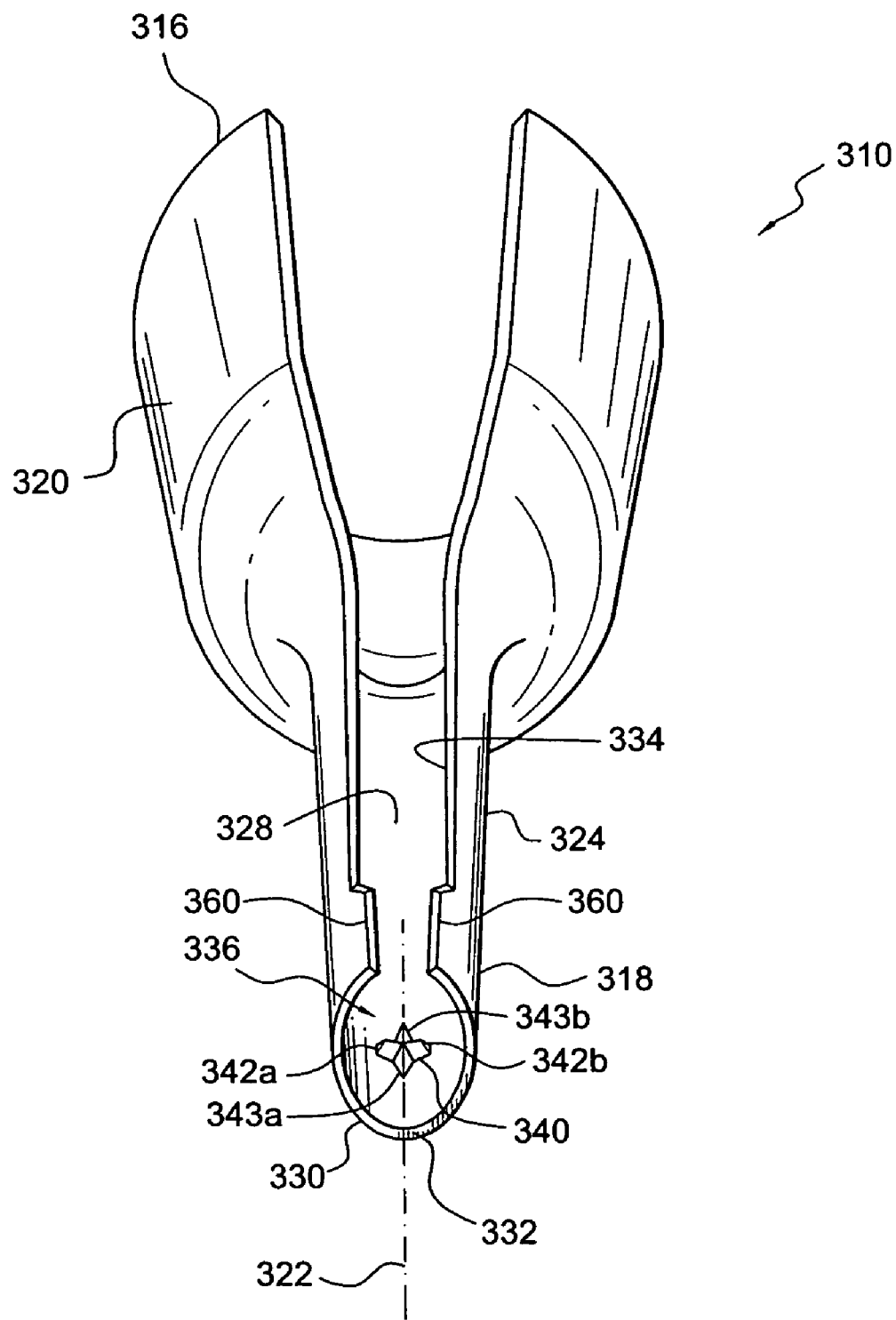

In accordance with yet a further embodiment of the present invention, and with reference to FIGS. 17 to 19, a cuffed-catheter removal device 310 is disclosed. As with the prior embodiments, the cuffed-catheter removal device 310 is designed to dissect the fibrous tissue off the cuff 312 of a tunneled dialysis catheter 314. Through implementation of the present cuffed-catheter removal device 310, removal time is significantly decreased. The cuffed-catheter removal device 310 also allows for catheter 314 removal through a preexisting pathway and precludes the need for a "cut down", utilizing a scalpel or other sharp instrument, so as to keep with a minimally invasive philosophy.

As with the prior embodiments discussed above, the cuffed-catheter removal device 310 includes a proximal end 316 and a distal end 318. The proximal end 316 generally includes an ergonomic handle 320 adapted for effectively allowing a practitioner to rotate the cuff-catheter removal device 310 about 360° or more so as to circumferentially dissect the cuff 312 and catheter 314 from the surrounding tissue. The ergonomic handle 320 is positioned at the proximal end 316 of the removal device 310 and is a generally elongated, cylindrical member shaped and dimensioned for gripping by a user of the device 310. The handle 320 extends along a longitudinal axis 346 that is obliquely oriented relative to the shaft 324 of the cuffed-catheter removal device 310. By orienting the handle 320 obliquely relative to the shaft 324, improved operation and functionality is achieved. The handle 320 allows a user to readily grasp the cuffed-catheter removal device 310 and rotate the same about the longitudinal axis 346 of the removal shaft 324 of the cuffed-catheter removal device 310.

In accordance with a preferred embodiment, the longitudinal axis of the handle extends at a 10 degree angle relative to the longitudinal axis of the shaft. However, and as those skilled in the art will appreciate, this angle may be increased, decreased, or the handle may be constructed in-line, and at no angle relative to the longitudinal axis of the shaft.

The distal end 318 of the cuff-catheter removal device 310 is generally composed of the shaft 324. The shaft 324 of the cuffed-catheter removal device 310 extends from the distal end 318 of the handle 320 and has a longitudinal axis 322 that is obliquely oriented with respect to the longitudinal axis 346 handle member 320. The shaft 324 is adapted to extend from the distal end 318 of the handle 320 of the cuffed-catheter removal device 310 to the catheter cuff 312 requiring removal. The shaft 324 is substantially C-shaped as it extends from its proximal end 316 secured to the handle 320 to its distal tip 330. As such, the shaft 324 may be thought of as a C-shaped shaft member 326 having a concaved recess 328 shaped and dimensioned for attachment and tracking along the exposed catheter shaft with the catheter shaft positioned within the concave recess 328.

As with the prior embodiments discussed above, and in accordance with a preferred embodiment, the dimensions are in keeping with the CVC shaft dimensions. As those skilled in the art will appreciate, there are varying CVC shaft dimensions, and, accordingly, there will also be varying cuffed-catheter device dimensions to fit associated CVCs. For example, the standard dialysis catheter diameters are 14 F to 16 F, while other catheters are 8 F to 12 F in diameter. Dimensions are to be kept in mind while optimizing the dimensions of the concave recess.

The leading, or distal, tip 330 of the shaft 324 is provided with a serrated or beveled edge 332 sharp enough to dissect the fibrous tissue, but blunt enough so as not to cause catheter 314 damage. In accordance with a preferred embodiment, the C-shaped shaft member 326 forms substantially all of the shaft 324 extending from the handle 320 to the distal tip 330 of the shaft 324 of the present cuffed-catheter removal device 310, although those skilled in the art will appreciate the length of the C-shaped portion may be varied to suit specific design needs. In fact, the C-shaped profile continues through the handle 320 in accordance with a preferred embodiment of the present invention. The extending length of the C-shaped shaft member 326 improves tracking of the exposed catheter 314 by allowing the catheter 314 to ride within the concave recess 328 for an extended length thereof as the cuffed-catheter removal device 310 is moved to a location of the cuff 312 requiring removal. It is contemplated in accordance with a preferred embodiment, that the entire length of the shaft 324, and ultimately the C-shaped shaft member 326, extending from the handle 320 will be approximately 4 cm to approximately 12 cm, and the concave recess 328 will extend the entire length of the shaft 324. As discussed above, the C-shaped shaft member is formed with a C-shaped cross section when viewed in the cross section defining the distal concave recess 328 of the shaft 324. By forming the C-shaped shaft member 326 in this manner, the distal end 318 of the cuffed-catheter removal device 310, in particular, the shaft 324, may readily track the exposed portions of the catheter 314 with the catheter 314 extending through the opening 334 of the concave recess 328 as the cuffed-catheter removal device 310 is moved along the catheter 314 toward the predetermined cuff 312 location requiring removal.

As with the prior embodiments, the opening 334 of the C-shaped shaft member 326, and concave recess 328, is preferably approximately 15% to approximately 50% of the circumference of the catheter 314 requiring removing. This circumference is sufficient for passage of the catheter 314 therethrough as the cuffed-catheter removal device 310 is moved along. With this in mind, the C-shaped shaft member 326 defines an arc of approximately 180° to approximately 300°, wherein the opening amounts to approximately 60° to approximately 180° of the entire circle defined at the distal end 318 of the cuffed-catheter removal device 310. In accordance with a preferred embodiment, the opening 334 slightly tapers inwardly adjacent to the distal end 318 of the cuffed-catheter removal device 310 with the inclusion of inwardly directed flanges 360 along the C-shaped shaft member 326 on opposite sides of the opening 334. This structure allows for more effective attachment to the catheter 314 while ensuring the distal tip 330 remains affixed during rotation.

The distal end 318 of the cuffed-catheter removal device 310 is further provided with an inner bead 336 adjacent the distal tip 330 of the C-shaped shaft member 326. The inner bead 336 extends inwardly within the concave recess 328. The inner bead 336 is generally provided with a sharpened edge improving removal of the cuff by engaging and incising the cuff for removal thereof.

More particularly, the inner bead 336 is formed along the inner surface 338 of the C-shaped shaft member 326 at a position centered along the arc defining the concave recess 328. The inner bead 336 is approximately 2 mm to approximately 20 mm from the distal tip 330 of the C-shaped shaft member 326. The inner bead 336 includes a central protrusion 340 extending into the center of the concave recess 328 a distance of approximately 1 mm to approximately 5 mm. Cutting members 342a, 342b extend from opposite sides of the central protrusion 340. The cutting members 342a, 342b extend in a direction substantially laterally to the central longitudinal axis 322 of the C-shaped shaft member 326 while also extending about the central longitudinal axis 322 of the C-shaped shaft member 326. The central protrusion 340 also includes a distally and proximally directed cutting member 343a, 343b bisecting the cutting members 342a, 342b. The inclusion of the inner bead 336 assists in the cuff removal process in two ways. First, the central protrusion 340 is shaped and dimensioned to engage the fibrous tissue that is attached to the distal edge of the cuff 312, allowing one to exert tension on the fibrous tissue by pulling the catheter 314 proximally once the inner bead 336 of the cuffed-catheter removal device 310 is properly positioned at the desired distal edge cuff position. With the fibrous tissue tensioned through the application of proximal pulling, the cuffed-catheter removal process is improved. In addition, the cutting members 342a, 342b, 343 are shaped and dimensioned to assist in cuffed-catheter removal by cutting through the fibrous tissue as the cuffed-catheter removal device 310 is rotated.

As those skilled in the art will appreciate, the present removal device 310 is utilized in the manner discussed above with regard to the previous embodiments.

In accordance with an alternate embodiment, it is further contemplated the shaft may be made from resilient materials, for example, a biocompatible polymer. As such, the shaft would be pliable allowing the opening to expand over the catheter shaft and then return to its original size once the shaft is placed over the catheter shaft.

With the foregoing in mind, the present invention provides a one-handed, ergonomic surgical instrument that is placed over the exposed catheter shaft and effectively passes through the subcutaneous tunnel while dissecting the fibrous tissue away from the cuff and catheter shaft distal to the cuff. It also allows catheter removal through the exit tunnel and precludes the need for surgical "cut down" thereby minimizing patient trauma and significantly decreases catheter removal time and provides a catheter removal option that does not require the use of a scalpel and associated "sharp" risk factors.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A cuffed-catheter removal device, comprising: a handle; a shaft extending from the handle, the shaft extending from the handle to a distal end of the cuffed-catheter removal device, at the distal end of the cuffed catheter removal device the shaft includes a C-shaped shaft member with a concave recess shaped and dimensioned for attachment and tracking along an exposed catheter shaft, and further including an inner bead adjacent to a distal tip of the C-shaped shaft member.

2. The cuffed-catheter removal device according to claim 1, further including a cutting edge at a leading end of the distal end of the cuffed-catheter removal device.

3. The cuffed-catheter removal device according to claim 2, wherein the cutting edge is a serrated cutting edge.

4. The cuffed-catheter removal device according to claim 1, wherein the C-shaped shaft member forms a substantial portion of the shaft.

5. The cuffed-catheter removal device according to claim 1, wherein the C-shaped shaft member has a diameter slightly larger than the shaft diameter of the cuffed-catheter to be removed.

6. The cuffed-catheter removal device according to claim 1, wherein the inner bead is formed along an inner surface of the C-shaped shaft member.

7. The cuffed-catheter removal device according to claim 1, wherein the C-shaped shaft member includes a slightly sharpened bevel formed along an interior surface of the C-shaped shaft member.

8. The cuffed-catheter removal device according to claim 1, wherein the C-shaped shaft member includes inwardly directed flanges adjacent the distal end of the cuffed-catheter removal device create an inward taper.

9. The cuffed-catheter removal device according to claim 8, further including a cutting edge at a leading end of the distal end of the cuffed-catheter removal device.

10. The cuffed-catheter removal device according to claim 9, wherein the C-shaped shaft member forms a substantial portion of the shaft.

11. The cuffed-catheter removal device according to claim 9, wherein the cutting edge is a serrated cutting edge.

12. The cuffed-catheter removal device according to claim 10, further including an inner bead adjacent a distal tip of the C-shaped shaft member.

13. The cuffed-catheter removal device according to claim 1, further including a central protrusion extending into a center of the C-shaped shaft member.

14. The cuffed-catheter removal device according to claim 13, wherein the central protrusion extends into the center of the C-shaped shaft member a distance of approximately 1 mm to approximately 5 mm.

15. The cuffed-catheter removal device according to claim 1, wherein the recess defines an opening, and the opening tapers inwardly at the distal end of the cuffed-catheter removal device.

16. The cuffed-catheter removal device according to claim 15, wherein the opening includes inwardly directed flanges on opposite sides of the opening.

17. A cuffed-catheter removal device, comprising:
a handle;
a shaft extending from the handle, the shaft extending from the handle to a distal end of the cuffed-catheter removal device, at the distal end of the cuffed-catheter removal device the shaft includes a C-shaped shaft member with a concave recess shaped and dimensioned for attachment and tracking along an exposed catheter shaft
an inner bead adjacent to a distal tip of the C-shaped shaft member, wherein the inner bead is formed along an inner surface of the C-shaped shaft member and the inner bead includes a central protrusion and cutting members extending from the opposite sides of the central protrusion.

18. The cuffed-catheter removal device according to claim 17, wherein the central protrusion of the inner bead extends into a center of the C-shaped shaft member a distance of approximately 1 mm to approximately 5 mm.

19. The cuffed-catheter removal device according to claim 18, wherein the bevel is formed along an interior surface of the C-shaped shaft member and protrudes at approximately a 45° angle relative to a longitudinal axis of the cuffed-catheter removal device.

20. The cuffed-catheter removal device according to claim 17, wherein the cutting members extend laterally relative to a longitudinal axis of the C-shaped shaft member.

21. The cuffed-catheter removal device according to claim 17, further including a distally directed cutting member.

22. A method for removing a cuffed-catheter from a body comprising:
providing a cuffed-catheter removal device comprising a handle and a shaft having a proximal end carried by the handle, a distal end spaced apart from the proximal end, and a recess extending through the shaft between the proximal end and the distal end for receiving the cuffed-catheter;
inserting the cuffed-catheter in the recess;
manipulating the handle so the shaft cuts body tissue away from the cuffed-catheter; and
removing the cuffed-catheter from the body.

23. The method according to claim 22, wherein the catheter includes a tissue in-growth cuff carried thereon; wherein the distal end of the cuffed-catheter removal device has a circumference greater than a circumference of the tissue in-growth cuff; and wherein manipulating comprises manipulating the handle so that a cutting edge of the shaft cuts body tissue away from the tissue in-growth cuff.

24. The method according to claim 22, wherein the shaft defines an opening therein, and wherein inserting comprises inserting the catheter in the recess of the shaft through the opening.

25. The method according to claim 22, wherein the distal end defines a serrated cutting edge.

* * * * *